US008337685B2

(12) United States Patent
Lee et al.

(10) Patent No.: US 8,337,685 B2
(45) Date of Patent: Dec. 25, 2012

(54) SERUM COMPONENTS THAT BIND TO THREAT AGENTS

(75) Inventors: William Edward Lee, Medicine Hat (CA); Robert Toussaint Poirier, Medicine Hat (CA); John Walter Cherwonogrodzky, Medicine Hat (CA)

(73) Assignee: Her Majesty the Queen in Right of Canada, as represented by the Minister of National Defence, Ontario (CA)

( * ) Notice: Subject to any disclaimer, the term of this patent is extended or adjusted under 35 U.S.C. 154(b) by 995 days.

(21) Appl. No.: 12/325,020

(22) Filed: Nov. 28, 2008

(65) Prior Publication Data

US 2009/0166200 A1     Jul. 2, 2009

Related U.S. Application Data

(60) Provisional application No. 60/991,372, filed on Nov. 30, 2007.

(51) Int. Cl.
*G01N 27/26*     (2006.01)
(52) U.S. Cl. ........................................ 204/451; 204/601
(58) Field of Classification Search ........................ None
See application file for complete search history.

(56) References Cited

U.S. PATENT DOCUMENTS

| | | | | |
|---|---|---|---|---|
| 2,002,019 A * | 5/1935 | Marzolf | .......................... | 261/153 |
| 5,139,630 A * | 8/1992 | Chen | .............................. | 204/451 |
| 5,228,960 A * | 7/1993 | Liu et al. | ........................ | 204/451 |
| 5,284,558 A * | 2/1994 | Linhardt et al. | ............... | 204/451 |
| 5,322,608 A * | 6/1994 | Karger et al. | ................. | 204/601 |
| 5,370,777 A * | 12/1994 | Guttman et al. | .............. | 204/452 |
| 5,490,909 A * | 2/1996 | Wang et al. | .................... | 204/452 |
| 5,571,680 A * | 11/1996 | Chen | .............................. | 435/7.4 |
| 5,599,433 A * | 2/1997 | Keo et al. | ....................... | 204/451 |
| 5,753,094 A * | 5/1998 | Alter et al. | ...................... | 204/451 |
| 5,922,184 A * | 7/1999 | Binder et al. | .................. | 204/452 |
| 5,958,202 A * | 9/1999 | Regnier et al. | ................ | 204/451 |
| 5,993,626 A * | 11/1999 | Landers et al. | ............... | 204/451 |
| 6,103,537 A * | 8/2000 | Ullman et al. | ................. | 436/526 |
| 7,297,244 B2 * | 11/2007 | Nouadje et al. | ............... | 204/451 |

(Continued)

OTHER PUBLICATIONS

Ailsa M. Campbell, Monoclonal Antibody and Immunosensor Technology, 1991, pp. 1-49, cover sheet and table of contents.*

(Continued)

*Primary Examiner* — Albert Navarro
*Assistant Examiner* — Ginny Portner
(74) *Attorney, Agent, or Firm* — Shelly Guest Cermak; Cermak Nakajima LLP

(57) ABSTRACT

Low molecular weight serum components (less than 10,000 m.w.), in vaccinated animals and a human subject who has been exposed to a threat agent inadvertently, bound to purified O-polysaccharide (OPS, a polymer of formamido-mannose) and a candidate of a threat agent, such as *Brucella suis* 145 vaccine is disclosed. These components formed a loose reversible precipitin with OPS in a high-salt borate-buffered agarose gel and bound to the candidate vaccine as observed by capillary electrophoresis. By using modified capillary electrophoresis, the invention also discloses the presence of two larger serum components, one similar in size to that of serum albumin and one resembles that of mannan-binding lectin, that bound to the vaccine. An indirect method for identifying vaccination is the presence of antibodies against *Brucella*-OPS-antibodies. ELISA, capillary electrophoresis and animal challenge studies showed that as high as 30% of the control animals did not require vaccination. These animals could have been exposed to cross-reactive cross-protective antigens naturally.

17 Claims, 9 Drawing Sheets

U.S. PATENT DOCUMENTS

| | | | |
|---|---|---|---|
| 2003/0054569 A1* | 3/2003 | Cheng et al. | 436/516 |
| 2003/0144582 A1* | 7/2003 | Cohen et al. | 600/316 |
| 2004/0058316 A1* | 3/2004 | Jensen et al. | 435/5 |
| 2005/0153346 A1* | 7/2005 | Schneider | 435/6 |
| 2005/0164302 A1* | 7/2005 | Robert et al. | 435/7.1 |

OTHER PUBLICATIONS

Jaskowski, Troy D. e tal, Clinical Vaccine Immunology, 2006, vol. 13(2), pp. 277-280, Detection of kappa and lamda chain monoclonal proteins in Human Serum: Automated immunoassay versus Immunofixation Electrophoresis.*

Landers, 1995, Clinical Chemistry, vol. 41(4), pp. 495-509.*

Arnold, J. N., et al., "The Glycasylation of Human Serum IgD and IgE and the Accessibility of Identified Oligomannose Structures for Interaction with Mannan-Binding Lectin," J. Immunol. 2004;173:6831-6840.

Bhogal, B. S., et al., "Production of Auto-anti-idiotypic Antibody during the Normal Immune Response," Cellular Immunol. 1986;101:93-104.

Cherwonogrodzky, J. W., et al., "A polysaccharide vaccine to enhance immunity against brucellosis," Arch. Med. Vet. XXVII, No. Extraordinaire, 1995, pp. 29-37.

Detilleux, P. G., et al., "Penetration and Intracellular Growth of *Brucella abortus* in Nonphagocytic Cells in Vitro," Infection and Immunity 1990;58(7):2320-2328.

Diaz, R., et al., "Radial Immunodiffusion Test with *Brucella* Polysaccharide Antigen for Differentiating Infected from Vaccinated Cattle," J. Clin. Microbial. 1979;10(1):37-41.

Dzwonek, A., et al., "Mannose-binding lectin in susceptibility and progression of HIV-1 infection in children," Antiviral Therapy 2006;11:499-505.

Franklin, R. D., et al., "Effects of Unfractionated and Low Molecular Weight Heparin on Antiphospholipid Antibody Binding in Vitro," Obstet, Gynecol. 2003;101:455-462.

Girardi, G., et al., "Heparin prevents antiphospholipid antibody-induced fetal loss by inhibiting complement activation," Nature Medicine 2004;10(11):1222-1226.

Mansour, M., et al., "Fungal Mannoproteins: The Sweet Path to Immunodoininance," ASM News 2003;69(12):595-600.

Nicholls, H., "The Camel Factor," NewScientist Oct. 6, 2007, pp. 50-53.

Niyonsaba, F., et al., "Human Defensins and Cathelicidins in the Skin: Beyond Direct Antimicrobial Properties," Critical Rev. Immunol. 2006;26(6):545-575.

Paré, J., et al., "Comparison of commercial enzyme-linked immunosorbent assays and agar gel immunodiffusion tests for the serodiagnosis of equine infectious anemia," Can. J. Vet. Res. 2004;68(4):254-258.

Tabona, P., et al., "Mannose binding protein is involved in first-line host defence: evidence from transgenic mice," Immunol. 1995;85:153-159.

Young, E. J., Brucellosis: Clinical and Laboratory Aspects Chapter 8, Clinical Manifestations of Human Brucellosis, pp. 97-126, CRC Press, Inc., Boca Raton, FL, US, 1989.

Yumuk, Z., et al., "Relevance of autoantibody detection to the rapid diagnosis of brucellosis," Diagnostic Microbiol. Infec. Dis. 2007;58:271-273.

* cited by examiner

Figure 2B

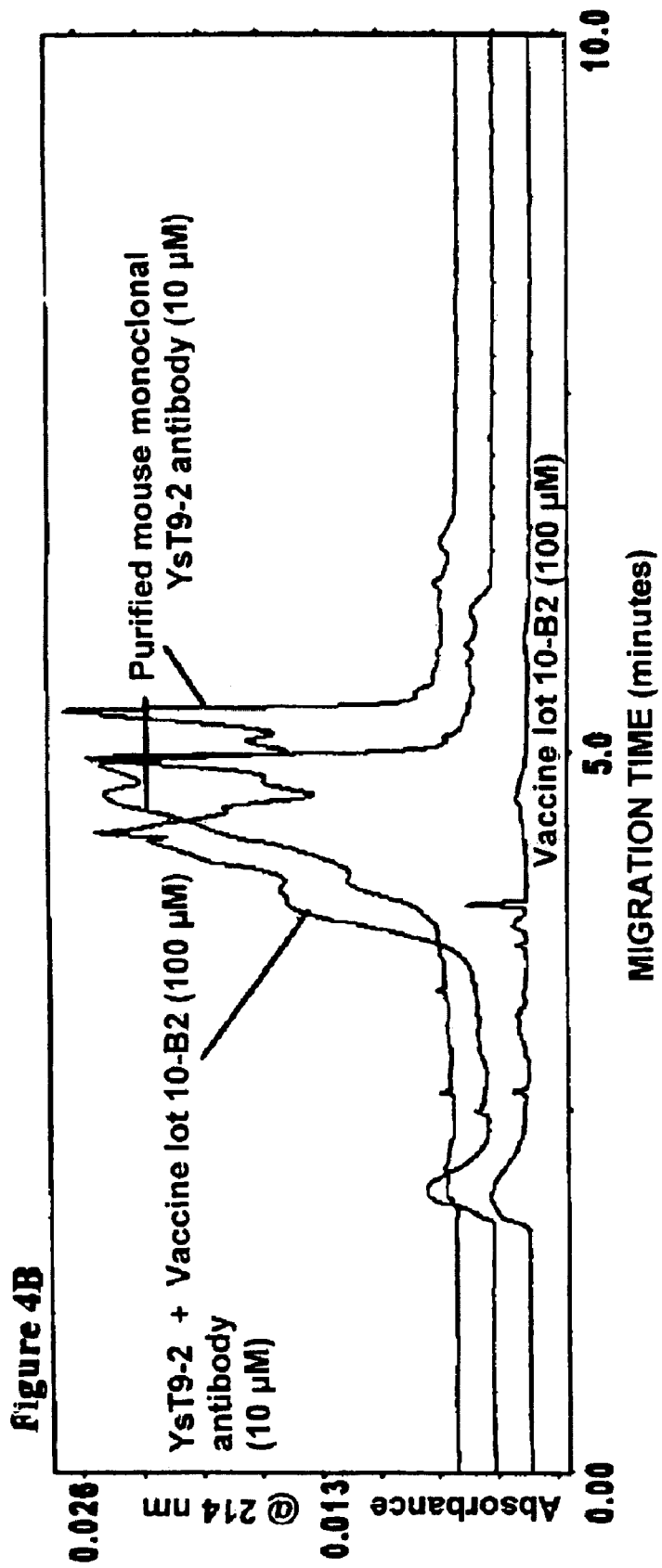

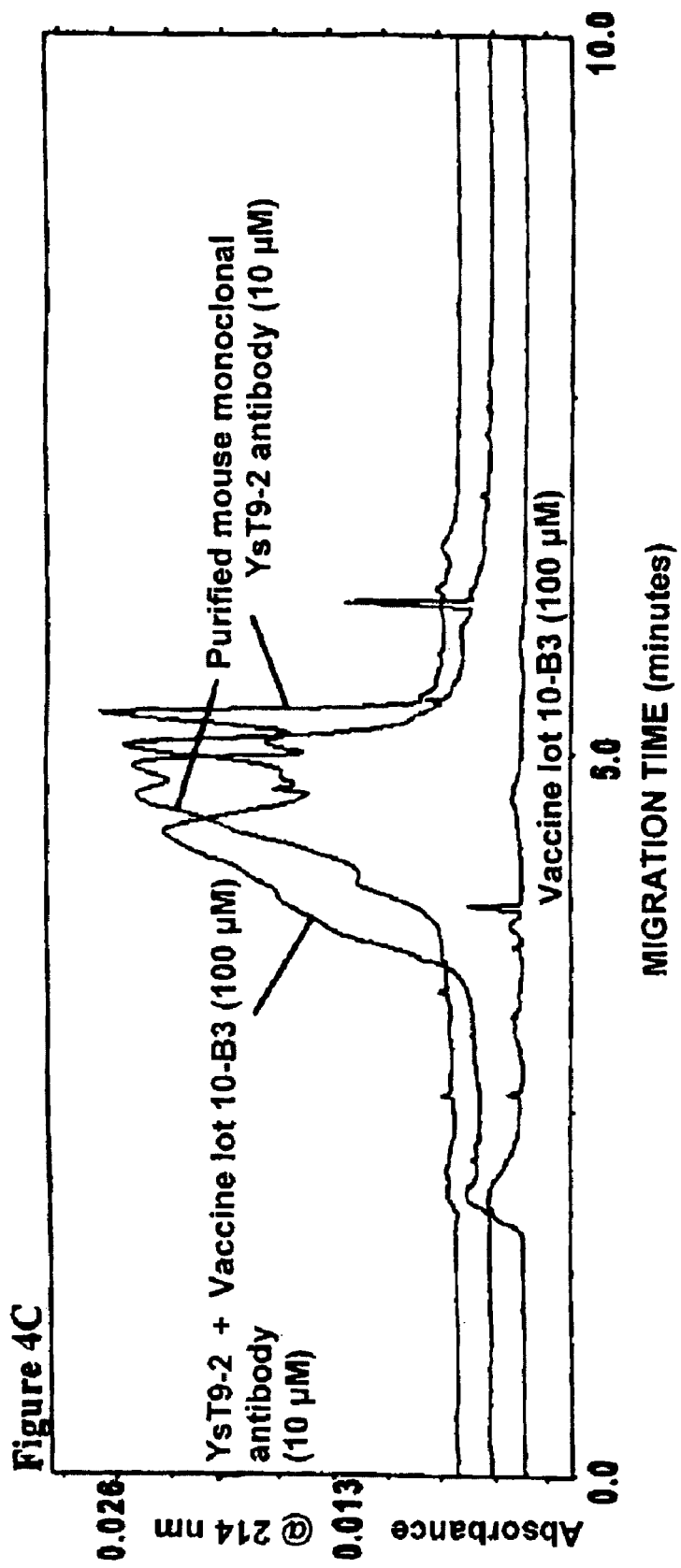

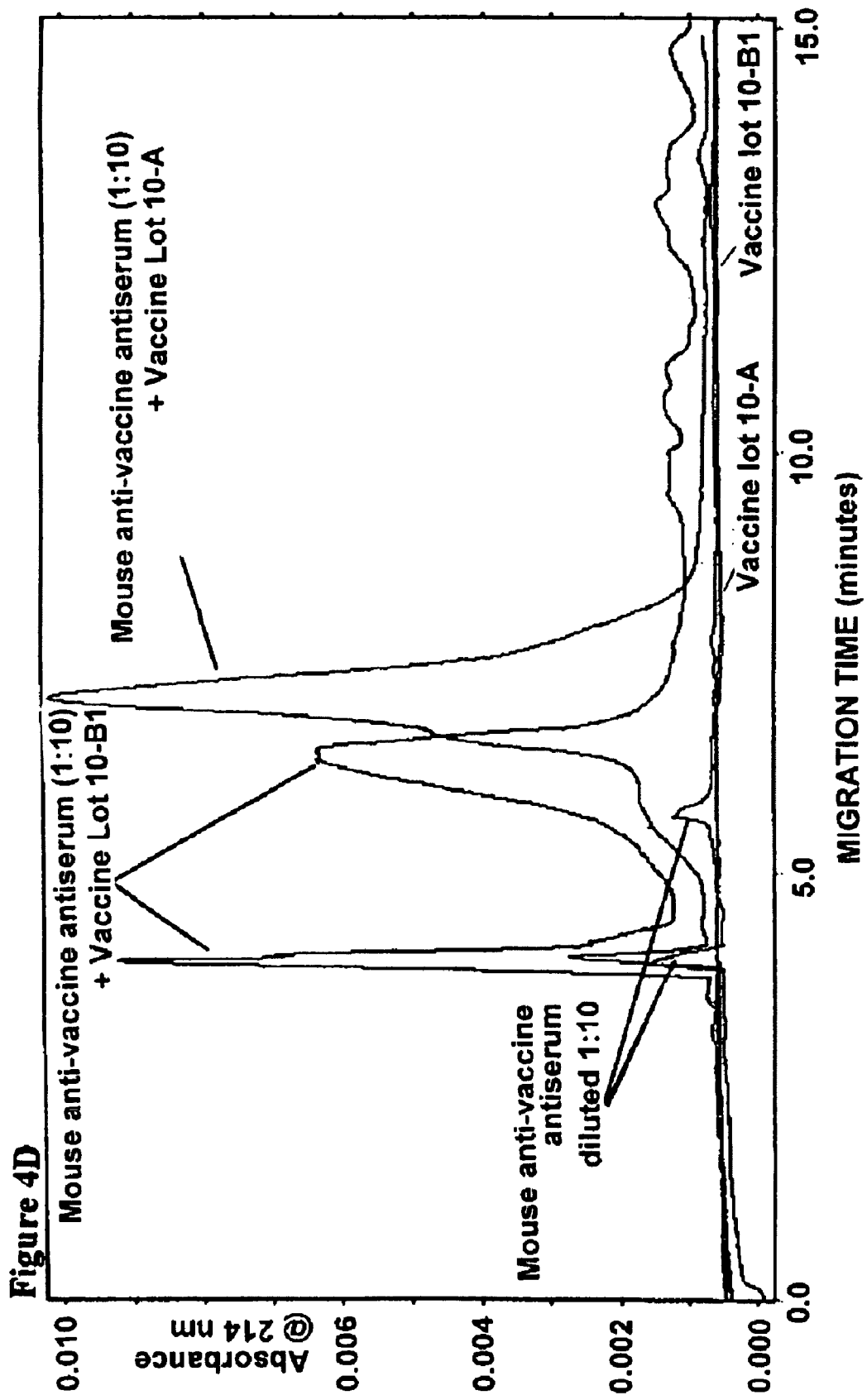

SERUM COMPONENTS THAT BIND TO THREAT AGENTS

This application claims priority benefit of U.S. Provisional Patent Application Ser. No. 60/991,372, filed Nov. 30, 2007.

FIELD OF THE INVENTION

This invention relates to the novel use of modified capillary electrophoresis to identify in vaccinated animals, as well as in a human subject exposed to vaccine components during the their preparation, serum components that bind to the polysaccharides of a candidate *Brucella suis* 145 vaccine.

BACKGROUND OF THE INVENTION

List of Prior Art Literatures

Diaz, R., Garatea, P., Jones, L. M., and Moriyon, I. 1979. Radial immunodiffusion test with a *Brucella* polysaccharide antigen for differentiating infected from vaccinated cattle. J. Clin. Microbiol. 10: 37-41.
Young, E. J. 1989. Clinical Manifestations of Human Brucellosis. In: Young, E. J., and Corbel, M. J. (ed.) Brucellosis: Clinical and Laboratory Aspects, CRC Press, Boca Raton, pp. 97-126.
Detilleux, P. G., Deyoe, B. L., and Cheville, N. F. 1990. Penetration and intracellular growth of *Brucella abortus* in non-phagocytic cells in vitro. Infect. Immun. 58: 2320-2328.
Cherwonogrodzky, J. W., and Di Ninno, V. L. 1995. A polysaccharide vaccine to enhance immunity against brucellosis. Arch. Med. Vet. (Chile). 27: 29-37.
Tabona, P., Mellor, A., and Summerfield, J. A. 1995. Mannose binding protein is involved in first-line host defence: evidence from transgenic mice. Immunology. 85: 153-9.
Mansour, M. K, and Levitz, S. M. 2003. Fungal mannoproteins: the sweet path to immunodominance. ASM News. 69:595-600.
Arnold, J. N., Radcliffe, C. M., Wormald, M. R., Royle, L., Harvey, D. J., Crispin, M, Dwek, R. A., Sim, R. B., and Rudd, P. M. 2004. The glycosylation of human serum IgD and IgE and the accessibility of identified oligomannose structures for interaction with mannan-binding lectin. J. Immunol. 173: 6831-40.
Pare, J., and Simard, C. 2004. Comparison of commercial enzyme-linked immunosorbent assays and agar gel immunodiffusion tests for the serodiagnosis of equine infectious anemia. Can. J. Vet. Res. 68: 254-258.
Niyonsabe, F., et al. 2006. Crit. Rev. Immunol. 26: 545-576.
Nicholls, H. 2007 New Scientist. 196: 50-53.
Dzwonek, A., et al. 2006. Antivir. Ther. 11: 499-505.
Yumuk, Z., et al. 2007. Diagn. Microbial. Infect. Dis. 58: 271-273.
Bhogal, B. S., et al. 1986. Cell Immunol. 101:93-104.

A bacterium, such as *Brucella*, could be a biological weapon, part of a rogue country's military program, a terrorist threat agent, an endemic disease that occurs in wildlife, or a common disease in a foreign country that puts peacekeeping forces at risk of infection. Although there is an uneasiness with the military or public with regards to their vulnerability to biological threats, with adequate medical protection and therapy, these threats could be rendered of little significance.

The Applicant's research facility has recently discovered an effective subcellular vaccine against brucellosis that protects mice from *Brucella abortus, B. melitensis* and *B. suis* as well as *Francisella tularensis* (U.S. Pat. Nos. 5,951,987 and 6,582,699). Applicant's working model for this vaccine is that it prevents threat agents from taking advantage of the mechanism by which mammalian cells destroy pathogens, such as fungi (Mansour and Levitz, 2003). For the latter, it is known that mannose receptors on mammalian cells bind the mannose on the surface of the fungi. The fungi are pulled inside, digested and hence destroyed (Mansour and Levitz, 2003). However, for some threat agents, notably those that are facultative parasites that thrive within the mammalian cells, rather than being a disadvantage this mechanism is an advantage to the threat agents. Many threat agents have mannose on their surface. The mannose would bind to the receptors as noted before, the threat agents would be pulled into the cell, but now instead of being destroyed the threat agent is able to grow inside the cell or express its toxic effects. This concept is supported by Applicant's U.S. Pat. No. 6,221,386 whereby "invasive liposomes" were created by adding *Brucella* polysaccharide to the formulation of liposomes, enhancing their penetration into mammalian cells. The vaccine induces an immunity which blocks the threat agent from attaching to the mammalian cell receptors. With the threat agent not being able to enter the cell, it will be destroyed by serum components such as complement or proteases.

The Applicant's laboratory has observed evidence of antibody expression following vaccination, but the significance of these is not convincing. An antibody response was observed when mice were vaccinated with O-polysaccharides ("OPS"). However, the greater the IgG or IgM levels in the sera, the worse the protection. Hence high dose vaccination was less effective than low dose, multiple doses of vaccine were less effective than a single dose, and components such as liposaccharides ("LPS") that had adjuvant effects lessened protection (Cherwonogrodzky et al., 1995). More recently, Applicant studied the long-term effects of the vaccine on anti-vaccine immunoglobulin expression in the sera of vaccinated mice. These were quantified on an ELISA that used the vaccine as antigen. IgM anti-vaccine expression was evident from wk 1-7, IgG anti-vaccine from wk 4-9, and anti-vaccine IgA or IgE was not detected. The expression of these was only for weeks, and yet protection against *Brucella* challenge lasted for 15 months.

That antibody expression was opposite to protection is understandable. Usually antibodies, raised against an infectious agent, will coat or "opsonize" the microbe or toxin which enhances the engulfment of the complexes by macrophages. Although the mechanism behind this enhanced engulfment is unclear, as some antibodies are glycosylated with mannose (Arnold et. al., 2004), it is likely that these would use the same mannose receptors that the threat agent has used to get inside the cell. The outcome would be that these antibodies would offer no therapeutic value in the defence against infection or toxicity. Indeed, as mannose-glycosylated antibodies would be counter-productive to immunity, one could speculate that it would be advantageous for the body to neutralize or clear these antibodies from the serum. It should be noted that arthritis, or the collection of auto-immune complexes of antibodies, is a common symptom of brucellosis (Young, 1989).

Another possible serum component, that would bind to the threat agent and block it from entering the cell, is the serum collectin "mannan-binding lectin" or MBL. MBL is a protein complex of about 300,000 m.w. that is secreted by the liver. The role of MBL appears to be to offer pro-active rather than reactive immunity. By being present in the sera of unexposed, non-immunized and unvaccinated hosts, it offers minimal broad-ranged protection against infectious agents (Tabona et al., 1995).

One could conclude from the above that, without an obvious humoral (serum) response to the vaccine noted in Applicant's patents referred hereto earlier, the exceptional protection against tested threat agents must be occurring from an induced cell-mediated (white blood cell) immunity. It is noted that cytokine expression is often used to assess the activation of macrophage in response to infection or exposure to microbial components. In Applicant's assessment of quantifying cytokine expression in vaccinated mice, a few did express cytokines that were detected in their sera, but this was sporadic and the majority of the mice did not express these (manuscript in preparation). Another argument against cell-mediated response is the reality of timing. Following vaccination, mice were protected from challenge for lengthy periods. It is unlikely that every cell in every tissue was active for 15 months against *Brucella*, especially since the vaccine dose was low (usually 1 µg of vaccine is given to a mouse, but Applicant also saw protection in mice given 10 nanograms of vaccine, results unpublished). One could speculate that the vaccine might be able to prime the cells, allowing these to respond to the antigens of an invading bacterium. However, this re-activation takes days while *Brucella* can infect and inactivate the mammalian cell's defenses in less than 2 hours (Detilleux et al., 1990).

Without the "usual list of suspects" to explain the immunity of vaccinated animals/humans, Applicant sought to identify, and partially characterize, other serum components that were involved with protection against threat agents.

SUMMARY OF THE INVENTION

This invention relates to the novel use of modified capillary electrophoresis to identify in vaccinated animals, as well as in a human subject exposed to vaccine components during their preparation, serum components that bind to the polysaccharides of a candidate *Brucella suis* 145 vaccine. The serum components identified are (i) a low molecular weight component, less than 10,000 m.w.; (ii) a component similar in size and elution time to albumin which has been termed "immuno-albumin" in this disclosure; (iii) a large component distinct from the two components noted in (i) and (ii) herein; and (iv) an antibody in the vaccinated mouse which binds to mouse monoclonal antibody anti-*Brucella*, also described as "anti-antibody" in this disclosure. There are multiple applications of the present invention, namely it provides a novel means of identifying the immune status of vaccinated animals or human subjects, determining if the latter require vaccination or that vaccination is unnecessary because such animals or human subjects are already protected through natural cross-protection, and assessing the cause of certain "auto-immune diseases" that are not caused by an immunity that has gone wrong for coping with infection.

According to the present invention, small molecular weight serum components (less than 10,000 m.w.), in vaccinated animals and a healthy human subject exposed to bacterial polysaccharides whom Applicant refers to as "an accidentally vaccinated human", bound to purified OPS (a polymer of formamido-mannose) and a candidate *Brucella suis* 145 vaccine. These components formed a loose reversible precipitin with OPS in a high-salt borate-buffered agarose gel and bound to the candidate vaccine as observed by modified capillary electrophoresis ("CE"). The modified CE also showed the presence of two larger serum components, one similar in size to that of serum albumin and one resemble that of mannan-binding lectin, that bound to the vaccine. The binding of the serum albumin-like component that bounds to the vaccine did not occur in the presence of heparin. An indirect method for identifying vaccination is the presence of antibodies against *Brucella*-OPS-antibodies. ELISA, CE and animal challenge studies showed that as high as 30% of the control animals did not require vaccination. As many infectious agents have the same or similar polysaccharide (notably the *E. coli* "hamburger disease" O:157,H:7, *Pseudomonas maltophilia, Salmonella landau, Yersinia enterocolitica* O:9, *Escherichia hermannii*, which occasionally contaminate and infect animals), the characteristic vaccine protection in unvaccinated control animals is likely due to exposure of cross-reactive cross-protective antigens from natural causes.

BRIEF DESCRIPTION OF THE DRAWINGS

FIG. 2B: (Human immuno-albumin against vaccine) Absorbance at 214 nm of vaccinated human serum, *B. suis* 145 vaccine, and vaccinated human serum co-incubated with *B. suis* 145 vaccine. (Note the larger peak for the latter at 6.5 min elution)

FIGS. 4A, 4B and 4C: (Identification of *B. suis* 145 vaccine "S" antigen) Absorbance at 214 nm of different *B. suis* 145 cell extractions co-incubated with mouse McAb YsT9-2. Fraction B1 is antigen shed by the bacterium, Fraction B2 is polysaccharide cleaved from the cell by 4% acetic acid, boiling water bath for 2 hours, Fraction B3 is polysaccharide cleaved from the cell by 4% acetic acid, autoclaving at 121 C, 15 psi of steam for 2 hours. (Note, McAb YsT9-2 bound to either "A" or "M" polysaccharides. Similar results were observed for McAb YsT9-3, which binds only to "A" polysaccharide, and McAb Bm3-8, which binds only to "M" polysaccharide. The three McAb bound to Fraction B2 and Fraction B3, but not Fraction B1. Fraction B1 is the most active vaccine preparation).

FIG. 4D: (Identification of *B. suis* 145 vaccine "S" antigen) Absorbance at 214 nm of *B. suis* 145 vaccinated mouse serum, vaccine Fraction B1 (shed antigen), vaccine Fraction A (Fraction B1, B2, B3 combined), and vaccinated mouse serum co-incubated with either Fraction B1 or Fraction A.

DETAILED DESCRIPTION OF THE INVENTION

Figure 1A:
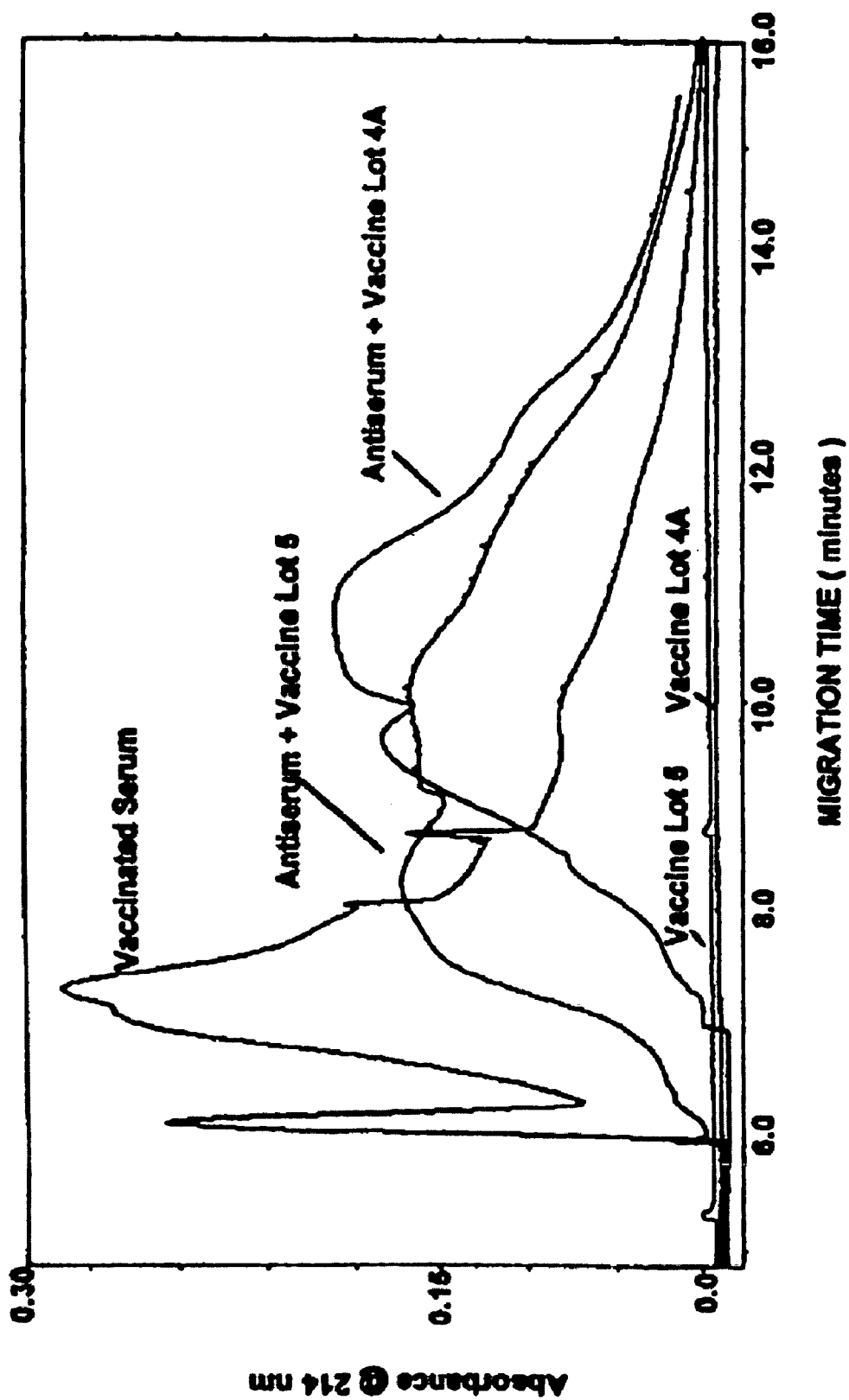
FIG. 1A: Absorbance at 214 nm of vaccinated mouse serum, *B. suis* 145 vaccine Lots 4A and 5, and co-incubated vaccinated mouse serum and vaccine preparations. (Note that the buffer and PEG source differed from FIGS. 2-5, hence the extended elution time of the antibodies and the antibody-vaccine complexes)

Materials and Methods
(a) Bacterial Culture

*Brucella suis* strain 145 (biovar 4, expresses "A" and "M" antigen) was acquired from the Animal Diseases Research Institute in Nepean, Ontario (ADRI—Nepean). Growth for vaccine preparation has previously been described (U.S. Pat. No. 6,582,699). Briefly, the bacterium was used to inoculate 100 ml of *Brucella* broth (BD and Co., Sparks, Md.) which was incubated overnight at 35° C., 5% $CO_2$, 90% humidity. Half a ml of the bacterial suspension was added to the surface of each of 400 sterile tissue culture flasks of 150 $cm^2$, 90 ml *Brucella* agar. The inoculum was dispersed by rolling glass beads (4 mm diameter) on the agar surface then transferring the beads to the next inoculated flask. The flasks were incubated as before but for 1 week.

(b) Vaccine Preparation

*Brucella suis* 145 vaccine was prepared as previously described (U.S. Pat. No. 6,582,699). In brief, 10 ml of 5% phenol, 1% saline was added to each flask, and the cells removed with glass beads by shaking/rolling the flask. The suspensions were pooled, then centrifuged (15,000× g, 30 min, 4° C., 30 min) and the cells washed with phenol-saline. The supernatant and cell washing were pooled to provide the source of vaccine Fraction B1. The cells were resuspended in 5 volumes (w/v) of 3% acetic acid and placed in a boiling water bath for 2 hr. The suspension was centrifuged as before and the cells were washed with 3% acetic acid. The supernatant and cell washing were pooled to provide the source of vaccine Fraction B2. To hydrolyze more of the O-polysaccharide, the cells were resuspended in 5 volumes of 3% acetic acid, this was autoclaved (121° C., 2 hr), centrifuged, washed with 3% acetic acid. The supernatant and cell washing were pooled to provide the source of vaccine Fraction B3. The antigens were concentrated into 90% phenol (10% water), precipitated in methanol with 1% sodium acetate trihydrate, dialyzed against phosphate buffered saline, enzyme digested (DNase, RNase, lysozyme, then proteinase K), proteins removed by precipitation with 02 M tricholoroacetic acid, which was removed by dialysis, debris removed by centrifugation, and the preparation freeze-dried. Vaccine Fraction A was made by combining B1+B2+B3.

(c) Sera from Vaccinated and Unvaccinated Control Mice

Mice (BALB/c female mice, 19-21 g when 35 days old, from St. Constant, Quebec) were cared for in accordance with the Canadian Council for Animal Care (CCAC). All procedures were reviewed and approved by the Animal Care Committee at DRDC Suffield (ACC—Suffield). The committee consists of veterinarians, scientists and lay people. The approved protocol was JC-99-07. For vaccination, mice were given 1 μg of vaccine in 0.1 m of sterile 0.85% saline given intramuscularly. These were allowed to rest for 4 weeks. Blood was collected either from the tail vein for small volumes (e.g. 0.1 ml) or from a heart puncture for larger volumes (e.g. 1 ml). For heparin treated-blood, the source of heparin was a (non-clotting) 10 ml blood-collection vaccutainer. One ml of sterile saline was added to the tube, heparin was extracted by use of a vortex, and a $1/10^{th}$ volume was added to 1.5 ml microfuge tubes that would receive the blood for processing (the amount of heparin in the blood samples was 15 units/ml). The samples were then spun in a microfuge (10,000× g, room temp, 1 min), and the serum saved. For non-heparin treated serum, blood was collected without heparin, clotted, centrifuged and the serum saved.

(d) Human Serum

Blood was collected from a researcher that had worked on *Brucella* polysaccharides for several years. It was speculated that the particular researcher might have been exposed to these antigens unintentionally through the course of the previous studies. Human serum was collected and used under approval of the Human Ethics Committee (HEC), a panel of physicians, scientists, lawyers and lay people, at DRDC Toronto. The protocol was HEC-01-002.

(e) Mouse Monoclonal Antibodies (McAb)

Mouse monoclonal antibodies (in mouse ascites fluid), raised against the antigens of either *Brucella* species or *Yersinia enterocolitica* O:9 (which are similar), was a generous gift from the National research Council of Canada (Ottawa).

(f) Capillary Electrophoresis (CE)

One of the strengths of capillary electrophoresis (CE) is that it can identify the binding of different components by the change in peak area and elution. Applicant's initial investigations did not require that these components to be isolated nor identified, either from the vaccine or from the serum.

Analysis was performed on a Beckman PACE system 5500 ID #306064. The run buffer was 50 mM boric acid (Fluka Chemicals, Switzerland), 2% polyethylene glycol 600 (Kodak, N.Y.) in distilled water, pH 7.0 (pH adjusted with 1 M NaOH). The sample diluent was deionized water. The separation was conducted on a 37 cm (length)×50 μm (internal diameter) uncoated column (Polymicro Technologies) utilizing an applied voltage of 20 kV, a sample injection of 20 seconds and a run time of 5.5-15 min. Assessment was by ultra-violet absorbance at 214 nm.

(g) Agar Gel Immunodiffusion (AGID)

Twenty ml of 10% NaCl, 0.01 M borate (pH 8.0, adjusted with HCl or NaOH), 1.2% agarose was melted in a boiling water bath. The contents were poured into a Petri plate (Fisher Scientific, Ottawa, Ont.), and allowed to cool. Shortly afterwards, wells were cut 1 cm apart with a cork borer 3 mm in diameter. *Brucella abortus* 1119-3 polysaccharide (10 mg/ml saline) was added to one well, undiluted serum from a cow (previously infected with *B. abortus*) was added to the other. Incubation was either at room temperature for about 1 hour or 37° C. for 24 hours. The formation of precipitin lines was assessed by eye.

Results and Discussions

As discussed earlier, Applicant previously studied a vaccine that protected mice from different species of *Brucella* (e.g. *Brucella abortus* strains 30 and 2308, *B. melitensis* 16M, *B. suis* 145). Subsequent research revealed that the vaccine was more effective than anticipated. For example:

- A single low dose (1 μg) protected mice from *B. suis* 145 challenge 15 months after vaccination.
- The more pathogenic the species or strain of *Brucella*, the more effective the vaccine (as determined by the difference in bacterial counts in the spleens of control unvaccinated mice and vaccinates).
- When mice were challenged with a million *B. suis* 145 cells given intraperitoneally, a week later the vaccinated mice had 10,000-fold less bacteria in their spleens than unvaccinated mice. By sacrificing groups of mice at different times over the course of 8 weeks, it was found that the vaccinated mice cleared any remaining bacteria (i.e. there were no relapses or recovery of bacterial numbers in the spleens).
- Partial protection was given to vaccinated mice challenged with 10-200 $LD_{50}$ of *Francisella tularensis* LVS.

It was observed that following vaccination, mice expressed IgG anti-vaccine titers for weeks 1-7 and IgM anti-vaccine titers for weeks 4-9. Although antibodies do play a role in reducing bacterial numbers at the onset of infection by binding to the bacterium and activating bactericidal serum complement, the effect is limited. Indeed, antibody coating of bacteria, or "opsonization", may lead to enhanced phagocytosis by macrophages which then allows the bacterium to enter and thrive inside the host cell. Applicant next examined cytokine expression as an indication that cell-mediated immunity might be taking place. Again, Applicant did not observe any evidence in its investigation that the latter was taking place. As the well-known classical mechanisms of immunity (antibodies, phagocytosis) against pathogens did not appear to be occurring, Applicant turned its attention to novel mechanisms.

Although the slope of *Brucella suis* 145 clearance from the spleens of vaccinated and unvaccinated control mice was the same, shortly after challenge the former had counts 10,000-fold less than the controls. Something was preventing the bacterium from entering the cells of the vaccinates.

One mechanism might be that the vaccine attaches to cell receptors or inserts into the mammalian cell's membrane, causing a cascade of responses that leads to enhanced cell-activity such as the digestion of foreign particles. Indirect evidence of this might be the observation that the red blood cells of vaccinated mice appear to be more sensitive to centrifugal forces than those taken from unvaccinated control mice. This enhancement of mammalian cell activity to clear pathogens may be taking place. Since this has already been taught in U.S. Pat. No. 6,444,210, it will not be pursued in the current patent application.

Applicant's observation that anti-*Brucella* antibodies were either below the level of detection or absent in vaccinated mice, as well as the serum of vaccinated mice offers passive immunity to unimmunized mice, suggested that there were other components in the serum that played a role in protection.

(a) "Picobodies"

(i) Agar Gel Immunodiffusion (AGID): For the detection of anti-*Brucella* antibodies in cattle, the use of high salt (10%) enhances the sensitivity of serological tests. Possibly this provides an environment that approaches a "salting out" effect, assisting the precipitation of complexes formed by the interaction of antigen and serum components. Another modification to a serological test is the incubation time for the AGID test. Incubation times for the AGID may range from 30 min (Diaz et al., 1979) to 48 hours (Pare and Simard, 2004).

In 1986, one of Applicant's researcher, Dr. John Cherwonogrodzky (a co-inventors herein) did a high-salt borate buffered AGID with purified OPS in one well (about 10,000 m.w.) and *B. abortus*-infected bovine serum in the other well. After one hour incubation at room temperature, a diffuse precipitin formed between the two wells. As this precipitin formed closer to the antigen well than the antiserum well, it suggested that the serum component(s) that took part in the precipitin formation were less than 10,000 m.w. Within a few hours the precipitin dispersed and was not evident. At 24 hr incubation at 37° C., another precipitin line was evident: more opaque, less diffuse and closer to the antiserum well. It appeared likely that there were two groups of serum components that interacted with OPS, a small molecular weight component less than 10,000 m.w., and a high molecular weight component (i.e. immunoglobulins). Candidates for the small molecular weight component may be defensins (Niyonsabe, 2006) or the recently publicized "nanobodies" (Nicholls, 2007). The traditional view of defensins is that they are expressed by epithelial cells such as the skin or intestinal lining, and are believed not to be present in the serum. Their role is to act as are broad-spectrum generic anti-microbial antibiotics. It has been reported that defensins are found in other sites of the body. This is only a response to trauma, a means of enhancing tissue repair, but unrelated to immunity.

Figure 1B:
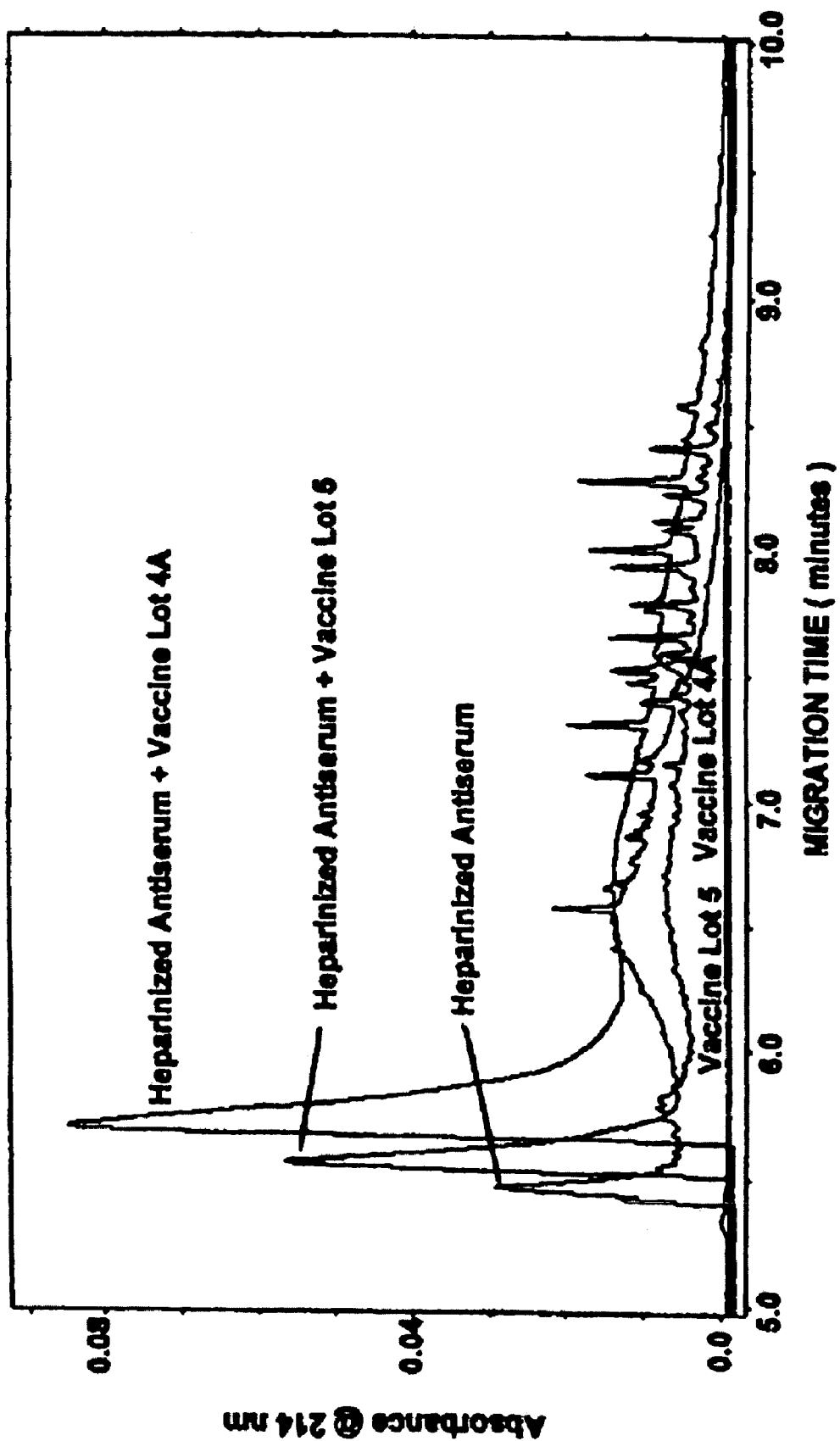
FIG. 1B: (Picobodies) Parameters are as for FIG. 1A, except that the vaccinated mouse serum was prepared from clotted blood for FIG. 1A, and from whole blood with heparin for FIG. 1B.

(ii) Modified Capillary Electrophoresis (CE): FIG. 1A shows Applicant's initial findings of the interaction of *B. suis* 145 vaccinated mouse antiserum and different vaccine lots. The more potent the vaccine lot (i.e. Lot 4A rather than Lot 5), the more the interaction and hence a shift to longer migration/elution times on the CE. In the elution profile of the vaccinated serum, and in other antiserum-antigen CE runs, peaks were observed at the start of the elution. Heparin is a highly charged glycoprotein that interferes with the binding of antibodies to complement (Girardi et al., 2004) or antigens (Franklin and Kutteh, 2003). FIG. 1B shows that heparin reduced much of the binding of serum components to the vaccine, but did little for the interaction of a serum component that eluted first from the column. Applicant believes that this heparin sensitive component, which has a large molecular weight, may be mannon-binding lectin, or MBL. MBL is thought to be produced constitutively to protect the very young from infections. The current understanding in the scientific community is that MBL cannot be enhanced through vaccination and indeed vaccination against tuberculosis only shows a lack of correlation with MBL. This serum lectin has also been referred to as an "acute phase protein" or a protein induced by injury, heart disease and inflammation rather than an immune response.

Further characterization of this serum component could not be continued due to the manufacturer's change in formulation of the polyethylene glycol 600. The change from branched to linear polymers of PEG prevented these initial peaks of serum components from being evident.

(b) "Immuno-Albumin"

Figure 2A:
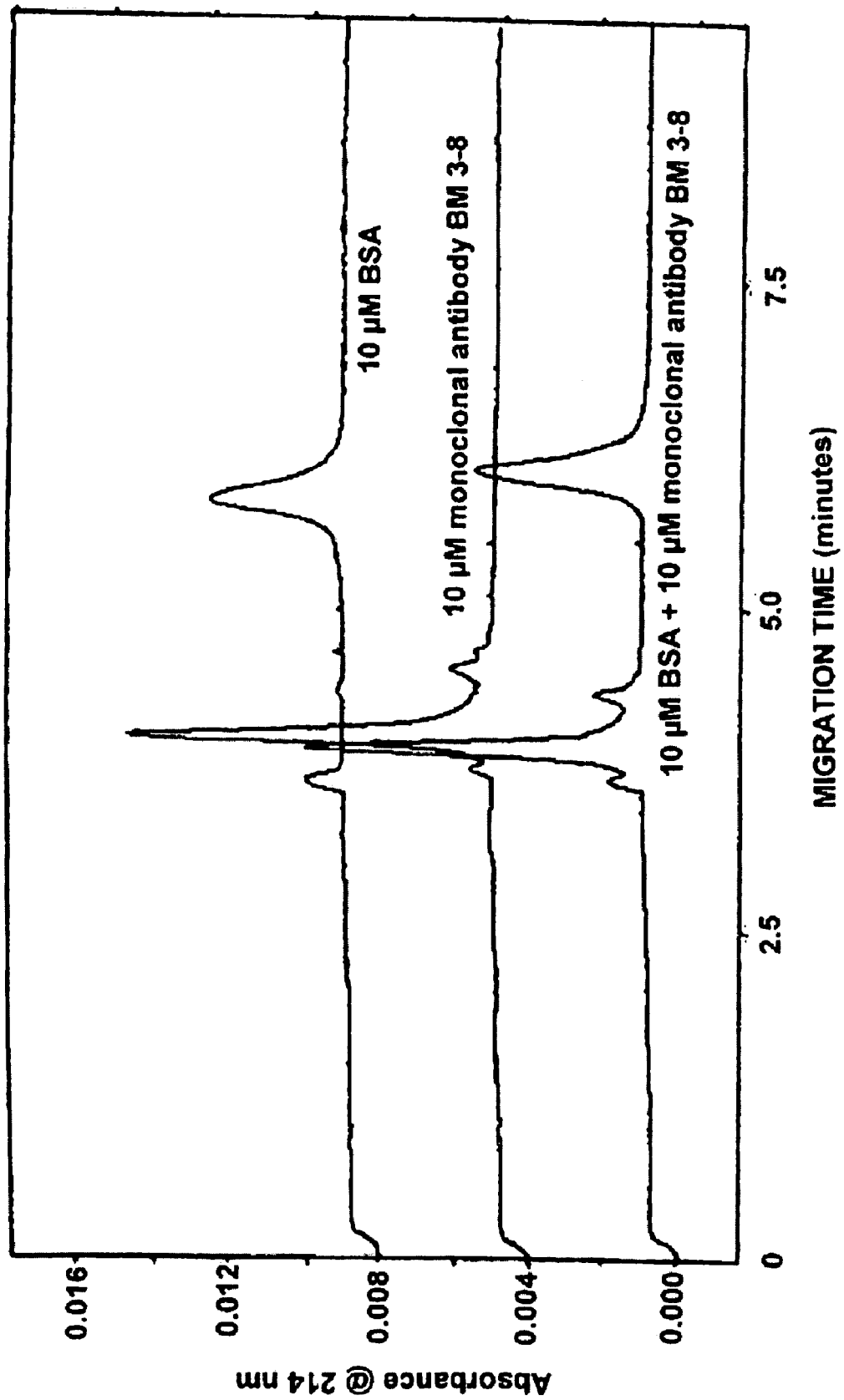
FIG. 2A: (Identifying albumin and antibody peaks) Absorbance at 214 nm of bovine serum albumin (BSA, at about 6 min elution), purified anti-*Brucella melitensis* OPS monoclonal antibody (McAb) BM 3-8 (at about 4 min elution), and BSA co-incubated with McAb BM 3-8.
Figure 2B:
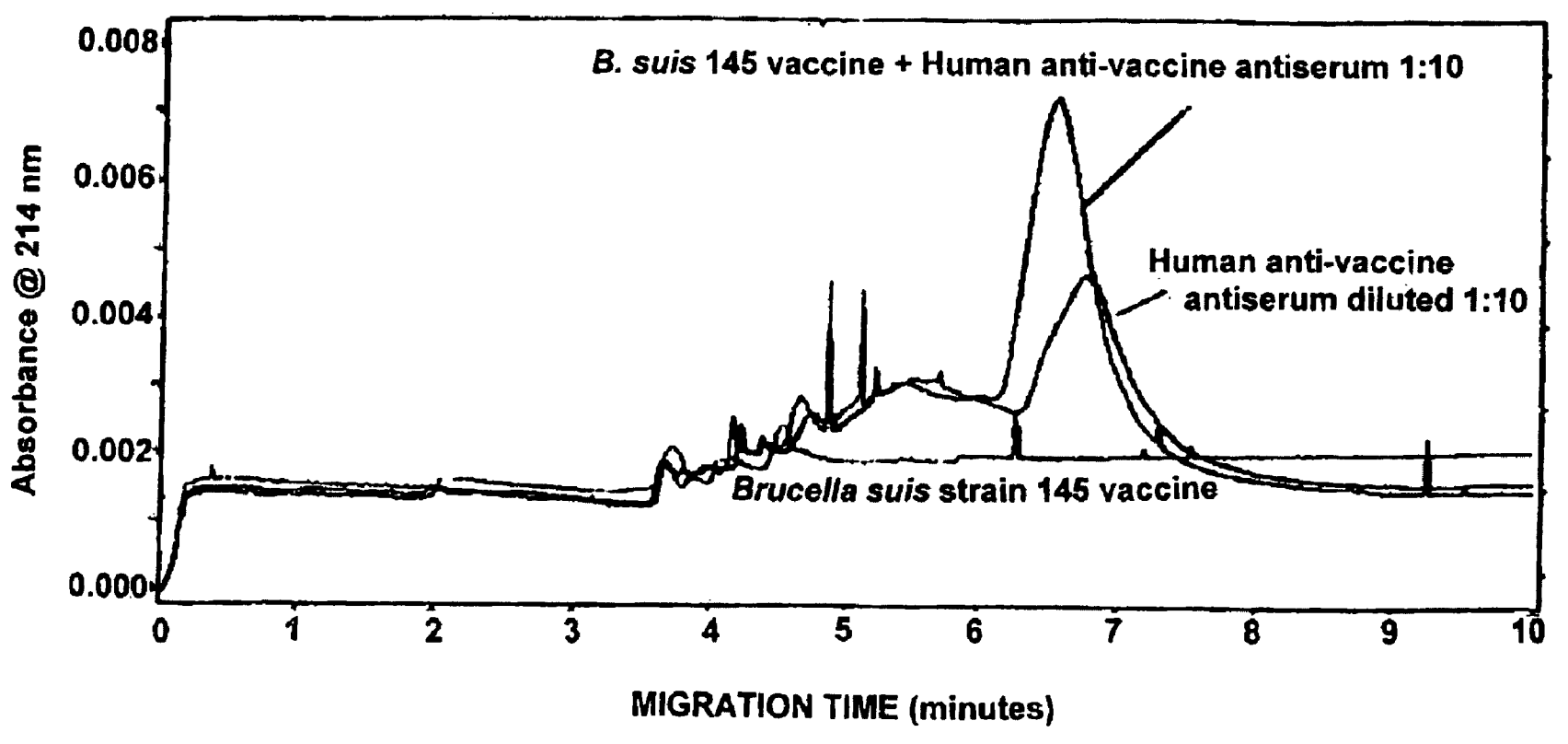

With CE analysis, Applicant observed other interactions between the anti-vaccine mouse serum and the vaccine. Notably, there was a serum component that interacted with the vaccine and that eluted in the same position as albumin, as noted in FIG. 2A. This evidence is the first report of albumin having immunological properties, of playing a direct role in immunity against infectious agents. For FIG. 2B, human antiserum (from one of Applicant's researcher who was exposed to *Brucella* components over several years) shows an albumin peak that increases in height when it is incubated with the vaccine. This albumin peak shift is also observed for vaccinated mouse serum co-incubated with the vaccine (data not shown).

Albumin is the most abundant protein in serum with a plasma concentration of 0.6 mM (40 mg/ml). Current understanding is that this protein has physiological and not immunological functions. For instance, it maintains homeostasis within the body, providing about 75% of the total osmotic pressure within our blood system. Survival of patients afflicted with stroke, trauma or organ malfunction depends on the level of albumin. Albumin binds toxic compounds such as bile acids, bilirubin and liver toxins. It is also a transport protein, carrying several micronutrients, vitamins, and iron throughout the body and transports drugs and antibiotics. Accordingly, the present discovery that albumin plays a role in binding to the *Brucella suis* 145 vaccine is totally unexpected.

(c) "Anti-Antibodies"

A common symptom of brucellosis is the occurrence of arthritis that results from an accumulation at the joints of anti-antibody complexes. Previously in this application, it was discussed that antibodies (especially those mannose glycosylated that would interact with the mannose cell receptors) might be counter-protective, causing opsonization and then enhanced entry of the pathogen into mammalian cells where it can then thrive. It would be logical if the vaccinate, that had an effective immune response, could clear the counter-protective antibody response. Autoantibodies have been observed for livestock and humans with brucellosis (Bhogal, 1986; Yumuk, 2007), contributing to the inhibition of the IgM and IgG immune response. Rather than an immune response that has become faulty, it is possible that this is instead a wise strategy of the host—removing antibodies that may lead to opsonization and enhanced entry of the bacterium into macrophages where it will infect and thrive.

The presence of antibodies against other antibodies is not new. In the 1930s, serum agglutinins were observed in rheumatoid arthritis and afterwards the role of antibody-antibody complexes that caused joint inflammation and pain was confirmed. This is commonly understood to be an unfortunate aberration when the immune system has gone wrong, which is contrary to the Applicant's findings that it is actually the correct response and part of the immunity to clear counter-productive antibodies. There is the view that anti-antibodies in brucellosis are counter-productive, a humoral immune abnormality. However, Applicant discovered that anti-antibodies in brucellosis are found in healthy vaccinates and removes anti-*Brucella* antibodies that are truly counter-productive.

Figure 3:
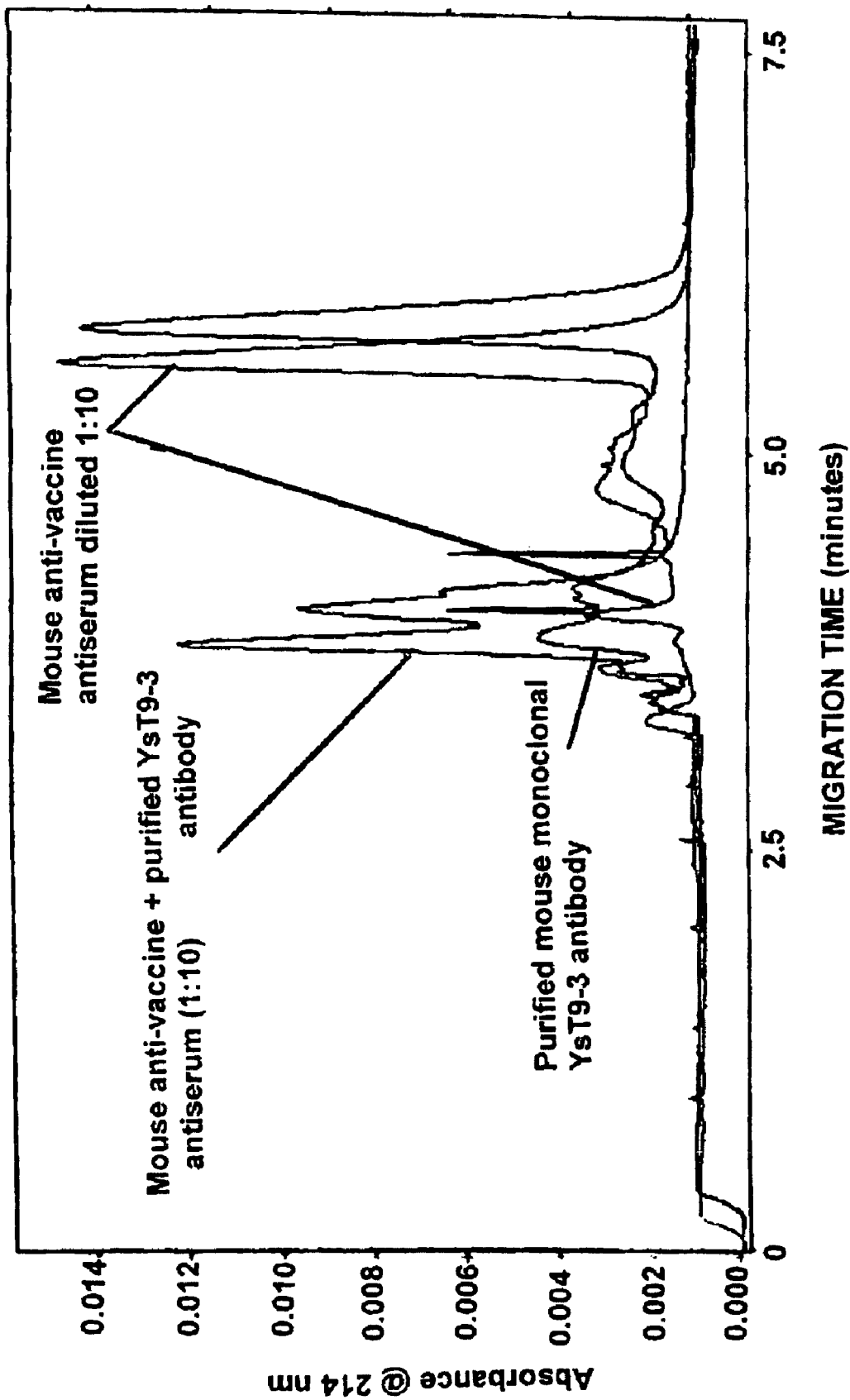
FIG. 3: (Anti-antibodies) Absorbance at 214 nm of purified mouse McAb YsT9-3, serum from a mouse vaccinated with *B. suis* 145 vaccine, and both co-incubated before electrophoresis. (Note enlarged peak at 4 min elution.)

FIG. 3 shows that this is occurring. The co-incubation of mouse vaccinate serum and purified YsT9-3 (anti-*Brucella abortus* "A" OPS) causes an enhanced peak to appear at around 3.7 minutes elution.

(d) Identification of the "S" Antigen in the Vaccine

In Applicant's U.S. Pat. No. 6,582,699, it was found that either the "A" antigen extracted from 1119-3 or the "M" antigen from *B. melitensis* 16M did not provide broad protection against different species and strains of *Brucella*. Only the vaccine extracted from *B. suis* 145 proved effective. After this patent award, subsequent studies clarified the location of the vaccine component(s) on the cell. *Brucella suis* 145 when grown on agar medium. After the cells were suspended and washed with phenol-saline, the supernatants were pooled, treated with weak acetic acid and heated in a boiling water bath for 2 hours. The antigen in the washings was noted as Fraction B1. The antigens (i.e. OPS) that were bound to the cell surface were then extracted by suspending the cells in weak acetic acid and heating in a boiling water bath for 2 hours. After centrifugation, the supernatant, containing cell-associated OPS, was noted as Fraction B2. To retrieve the remaining OPS, the cells were again resuspended in weak acetic acid and then autoclaved (121° C., 15 psi, 2 hours). After centrifugation, the supernatant was noted as Fraction B3. The polysaccharides were further enriched/purified by enzyme digestions and the removal of proteins by trichloroacetic acid. Animal challenge studies showed that although Fractions B2 and B3 did provide protection against *B. suis* 145, the most potent and consistent was Fraction B1.

Figure 4A:
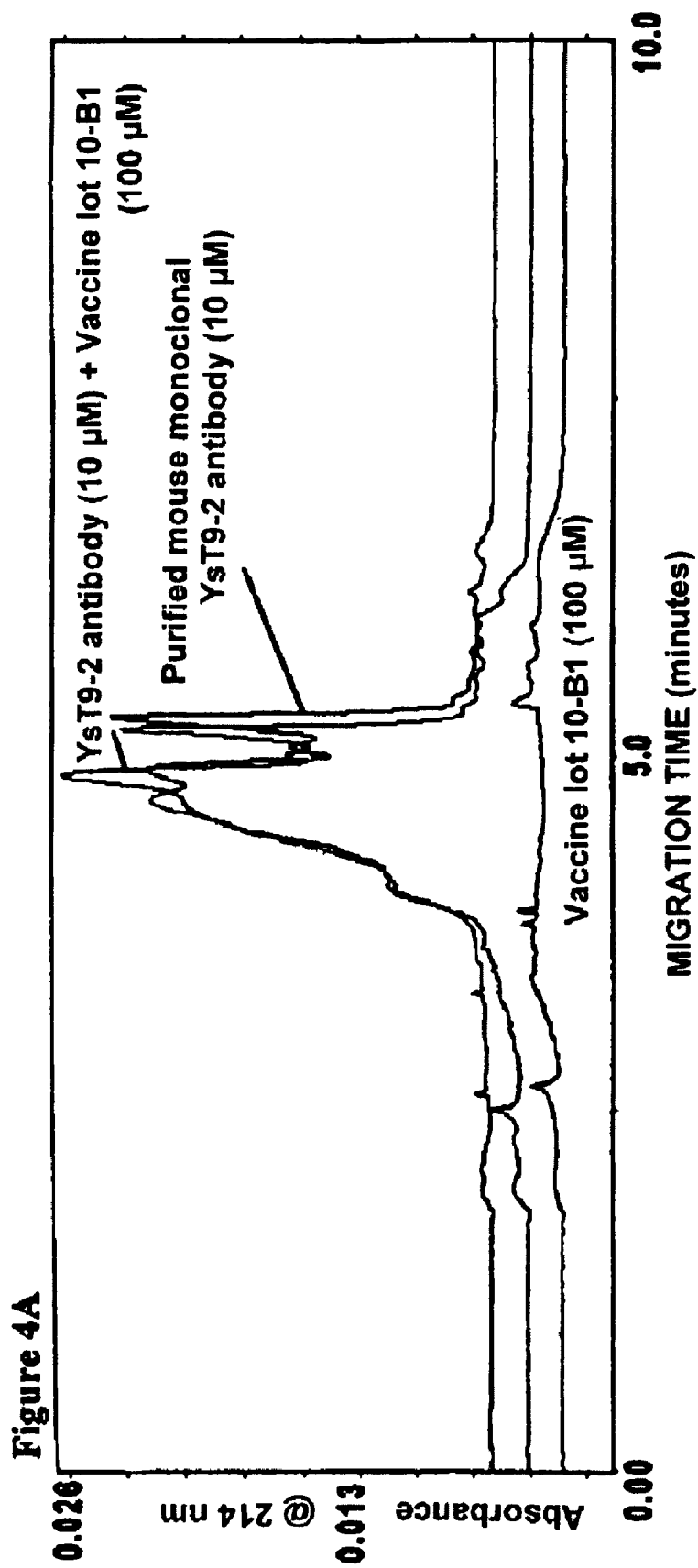

*B. suis* 145 expresses both the "A" and "M" antigens. The different vaccine fractions (B1, B2, B3) were co-incubated with mouse McAbs (YsT9-3 is anti-"A", Bm3-8 is anti-"M", YsT9-2 is anti-"A/M", as results were the same with the different McAbs, only that for Yst9-2 is presented) and eluted through CE. Although none of these recognized Fraction B1, the most potent vaccine component, (see FIG. 4A), all these recognized the cell-associated OPS in vaccine Fractions B2 and B3 (see FIG. 4B and FIG. 4C). In contrast, serum from vaccinated mice recognized either Fraction B1, or vaccine A which is prepared by combining Fractions B1+B2+B3 (see FIG. 4D). This gives further evidence that a key component in the vaccine preparation is an, as yet unidentified, antigen "S". As this was deducted in Applicant's previous U.S. Pat. No. 6,582,699, Applicant does not make any additional claims for antigen "S" herein but use these findings to support the usefulness of CE for the identification of immune status of vaccinates or the potency of vaccine lots.

The Applicant has observed limitations to the immune response to the vaccine in mice and a human. Due to a problem in the watering of vaccinated mice, these were dehydrated for a few days until this was corrected. Upon challenge with *B. suis* 145, the response was exceptional in that these animals were not protected from infection. In another circumstance, as noted in FIG. 2B, a researcher from Applicant's facility, who had been exposed to *Brucella* antigen over several years of study, had serum components that bound to the vaccine. However, when the researcher was given the annual anthrax vaccine booster (and they had received this over several years), no such serum component binding could be found (short note in preparation). It appears that the immune response is a very dynamic, variable mechanism that can redirect its activity to address stress or the presentation of some antigens. Modified CE technology would be useful in providing insight into the immunity animals/humans and the level of protection against certain diseases. Applicant has also noted that just as the researcher had unknowingly been exposed and vaccinated to *Brucella* antigens, so some unvaccinated control mice have likely been exposed to cross-reactive cross-protective bacteria, accounting for their IgG/IgM titres against the vaccine and protection (in some groups as high as 30%) from *B. suis* 145 challenge.

It is to be understood that the embodiments and variations shown and described herein are merely illustrative of the principles of this invention and that various modifications may be implemented by those skilled in the art without departing from the scope and spirit of the invention.

In addition, the List of Prior Art Literatures referred to in the Background of the Invention section is incorporated by reference herein.

In summary, the modified CE of the instant disclosure can be used to identify serum components that bind to threat agents. In practical terms, valuable and timely applications can be used to assess first responders (e.g. Hazmat team entering a terrorist scene) or military personnel (e.g. NBC response team). In some instances, the assays (e.g. CE, ELISA) can be used to determine which military personnel may not require vaccination since they may have been sufficiently protected to be deployed immediately. In times of pandemics, this information could also conserve on limited vaccine stocks, offering these only to those requiring protection.

What is claimed is:

1. A method for identifying in the serum of test subjects serum components which bind to a threat agent, said method comprising:
   a) conducting capillary electrophoresis with an ultra-violet wavelength absorbance monitor on said serum of said test subjects,
   b) identifying said serum components present in said serum by identifying peptide bonds in said serum by measuring absorbance at 214 nm of the ultra-violet wavelength,
   c) identifying said serum components which bind to said threat agent by identifying shifts in peak height and elution time between capillary electrophoresis results from said test subjects, wherein a large positive change in peak height and/or a longer elution time indicates binding of said serum component to said threat agent;
   wherein said threat agent is *Brucella*.

2. The method as defined in claim 1, wherein said test subjects are vaccinated animals or humans.

3. The method as defined in claim 1, wherein said threat agent comprises subunits of lipopolysaccharide and polysaccharide from *Brucella*.

4. The method as defined in claim 1, wherein one of said serum components is a protein and has a molecular weight of less than 10,000.

5. The method as defined in claim 1, wherein one of said serum components is albumin with binding affinity to the threat agent.

6. A method for determining the immune status of either a vaccinated or non-vaccinated animal or human subject comprising the method as defined in claim 1, and further comprising the identifying of serum components which bind to threat agents in a non-vaccinated animal or human subject indicates that said subject was likely inadvertently exposed to cross-reactive, cross-protective antigens similar to that of the threat agent.

7. The method as defined in claim 1, wherein one of said serum components is an anti-antibody.

8. The method as defined in claim 7, wherein said anti-antibody is against an antibody against said threat agent.

9. The method as defined in claim 8, wherein said antibody against the threat agent is an anti-*Brucella* antibody.

10. The method as defined in claim 9, wherein said anti-*Brucella* antibody is a monoclonal anti-*Brucella* antibody.

11. The method as defined in claim 1, wherein said test subjects comprise control naïve mice, *Brucella* polysaccharide-vaccinated mice, and a human exposed to a *Brucella* polysaccharide vaccine.

12. The method as defined in claim 1, wherein threat agent comprises polysaccharides extracted from *Brucella*.

13. The method as defined in claim 12, wherein said polysaccharides extracted from *Brucella* are vaccine candidates against *Brucella*.

14. The method as defined in claim 1, wherein said capillary electrophoresis uses a buffer system which comprises boric acid, 2% polyethylene glycol 600 at pH 7.0.

15. The method as defined in claim 14, further comprising diluting said serum 1:10 in said buffer system.

16. The method as defined in claim 14, wherein said buffer system comprising 50 mM boric acid and 2% polyethylene glycol 600 at pH 7.0, wherein said pH is adjusted with 1M NaOH.

17. The method as defined in claim 1, wherein one of said test subjects is a non-vaccinated animal or human that may have been exposed to a similar threat agent.

* * * * *